US012653741B2

(12) United States Patent　　　　(10) Patent No.:　US 12,653,741 B2

Grindstaff et al.　　　　　　　　　(45) Date of Patent:　Jun. 16, 2026

(54) PATIENT POSITIONING SYSTEM

(71) Applicant: DeRoyal Industries, Inc., Powell, TN (US)

(72) Inventors: Rex Allen Grindstaff, Wartrace, TN (US); Angela J. Schubert, Knoxville, TN (US); Phillip David Peery, Sweetwater, TN (US); Albert Pendleton Gillespie, III, Jacksboro, TN (US); Timothy James Grassi, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 334 days.

(21) Appl. No.: 18/237,438

(22) Filed: Aug. 24, 2023

(65) Prior Publication Data

US 2023/0390134 A1　　Dec. 7, 2023

Related U.S. Application Data

(63) Continuation-in-part of application No. 17/747,527, filed on May 18, 2022, now Pat. No. 11,771,609, which is a continuation of application No. 17/068,091, filed on Oct. 12, 2020, now Pat. No. 11,364,166.

(51) Int. Cl.
　　*A61G 7/10*　　　　(2006.01)
　　*A61F 5/37*　　　　(2006.01)
　　*A61G 13/12*　　　(2006.01)
(52) U.S. Cl.
　　CPC .......... *A61G 7/1057* (2013.01); *A61F 5/3769* (2013.01); *A61G 13/12* (2013.01); *A61G*

*13/1235* (2013.01); *A61G 13/126* (2013.01); *A61G 2200/32* (2013.01)

(58) Field of Classification Search
None
See application file for complete search history.

(56) References Cited

U.S. PATENT DOCUMENTS

2016/0008194 A1 * 1/2016 Ponsi ....................... A61G 7/10
　　　　　　　　　　　　　　　　　　5/81.1 HS
2016/0279007 A1 * 9/2016 Flatt ..................... A61G 13/126
2017/0112655 A1 * 4/2017 Giap ................... A61G 7/1023

* cited by examiner

*Primary Examiner* — Adam C Ortiz
(74) *Attorney, Agent, or Firm* — Luedeka Neely, P.C.

(57)　　　　　ABSTRACT

A patient positioning system configured for positioning and supporting a patient against movement on an operating table, the positioning system including a pair of arm positioners each configured to be positionable about an arm of the patient when the patient is lying on the operating table, each of the arm positioners provided as a sheet material configured to be wrapped around one of the arms of the patient to position each of the arm positioners to snugly envelope one of the arms and having releasable fasteners to maintain the arm positioners in the wrapped configuration; and an elongate lift sheet configured to extend across the operating table and underneath the back of the patient, the lift sheet being positioned to have opposite ends thereof wrapped over and around the arm positioners and tucked back under the lower back or sacrum of the patient to securely and snugly hold the lift sheet around the arm positioners and restrain the arms of the patient.

4 Claims, 9 Drawing Sheets

PATIENT POSITIONING SYSTEM

FIELD

The present disclosure relates to devices for positioning and restraining patients. More particularly, the disclosure relates to a patient positioning system for positioning a patient on an operating table in a steep Trendelenburg position or like steep position and to better support the patient on the table and prevent slipping or movement of the patient relative to the operating table.

BACKGROUND

Improvement is desired in devices for positioning and restraining patients on an operating room table. In particular, improvement is needed in devices for positioning a patient on an operating table in multiple Trendelenburg positions or Lateral Oblique positions. In these positions the patient is maintained at a steep angle greater than about 30 degrees. These positions are desirable for various medical procedures.

In the Trendelenburg position, the patient is flat on the operating table and the table is angled along its length axis so that the feet of the patient are vertically higher than the head of the patient.

The Reverse Trendelenburg position is the same, except the table is angled so that the head of the patient is vertically higher than the feet of the patient.

In Lateral Oblique positions the patient is positioned on the table to be tilted laterally to one side.

As will be appreciated, it becomes difficult to securely restrain a patient against movement and in a desired position in steep angle positions.

SUMMARY

The above and other needs are met by a patient positioning system configured for positioning and supporting a patient against movement on an operating table.

In one aspect, a patient positioning system according to the disclosure includes a pair of arm positioners each configured to be positionable about an arm of the patient when the patient is lying on the operating table.

Each of the arm positioners provided as a sheet material configured to be wrapped around one of the arms of the patient to position each of the arm positioners to snugly envelope one of the arms and having releasable fasteners to maintain the arm positioners in the wrapped configuration.

An elongate lift sheet is configured to extend across the operating table and underneath the back of the patient, the lift sheet being positioned to have opposite ends thereof wrapped over and around the arm positioners and tucked back under the lower back or sacrum of the patient to securely and snugly hold the lift sheet around the arm positioners and restrain the arms of the patient.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
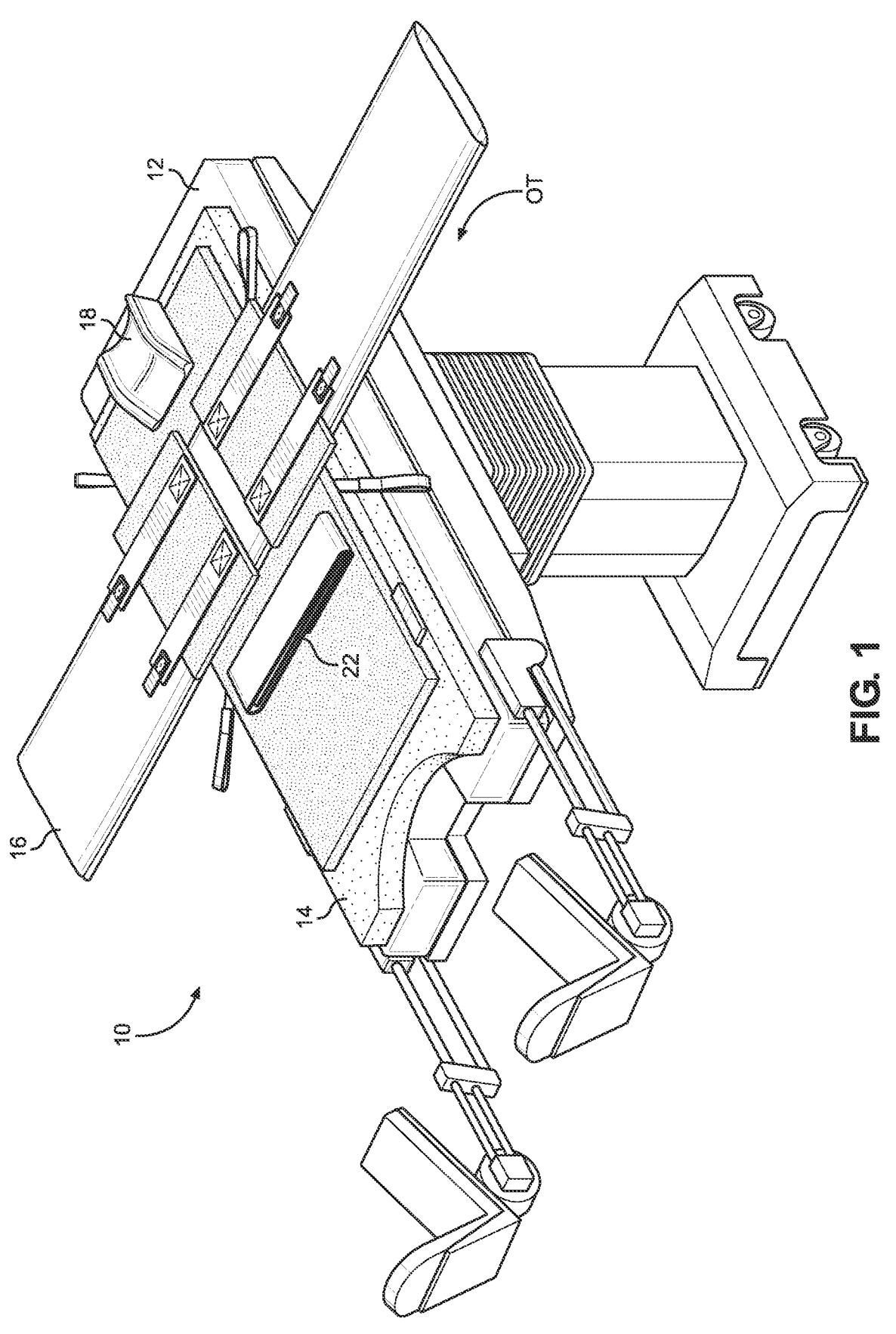
FIG. 1 is a perspective view showing a patient positioning system according to the disclosure installed on an operating table.
Figure 2:
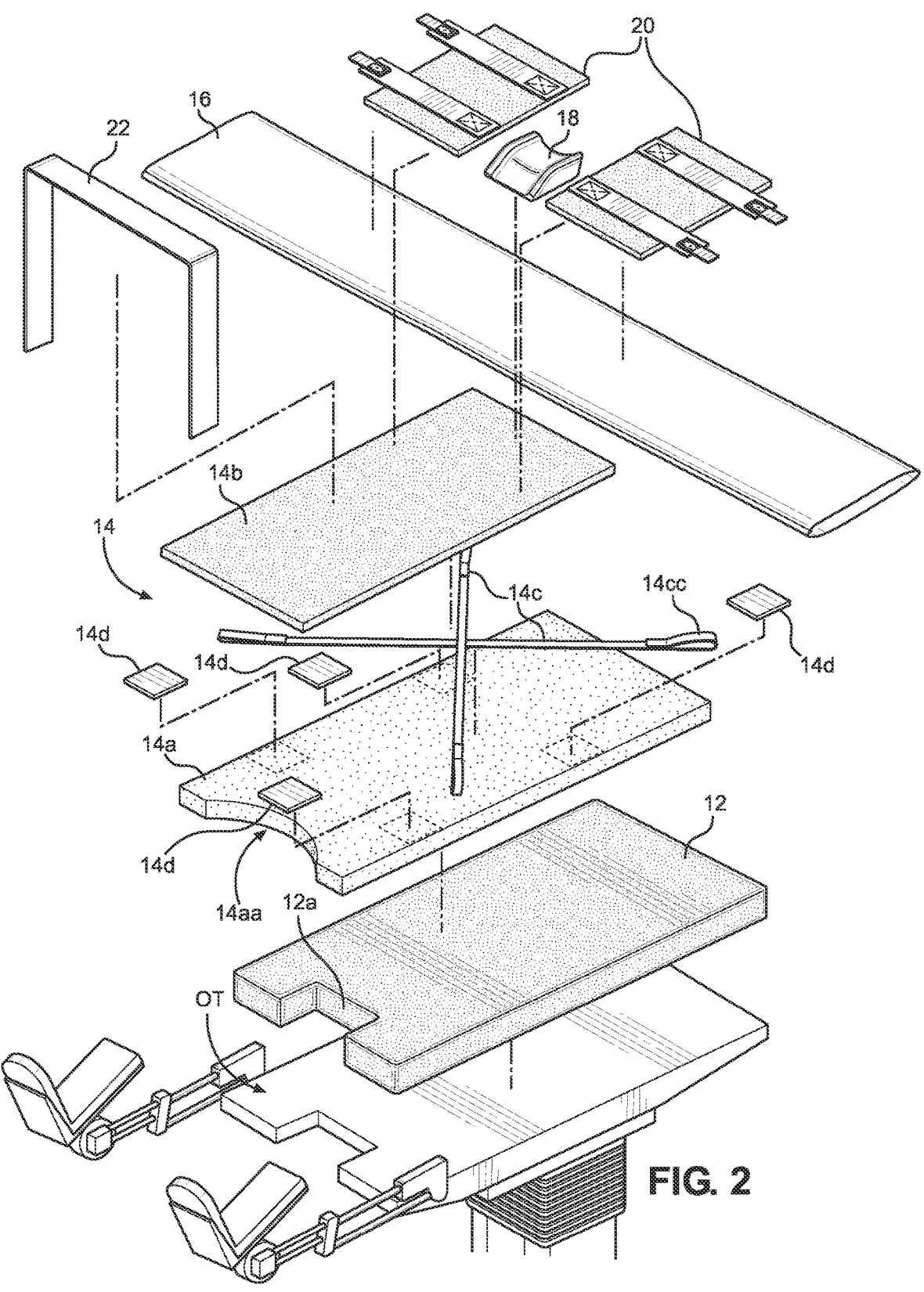
FIG. 2 is an exploded view of FIG. 1.

With initial reference to FIGS. 1 and 2, the disclosure relates to a patient positioning system 10 configured for positioning and supporting a patient P. The system 10 is particularly configured for supporting the patient P against movement on an operating table OT, including when the operating table OT is oriented to position the patient P at a steep angle. The components of the system 10 are also provided to be aesthetically pleasing to provide a visually appealing appearance.

In a preferred embodiment, the positioning system 10 includes a mattress pad base 12, a positioning pad 14, a lift sheet 16, a head positioner 18, a pair of arm positioners 20, and a body strap 22. It will be appreciated that the components may be used alone or in various combinations to position a patient. However, the use of all the components has been observed to yield the most stability against movement.

The operating table OT is a conventional operating table of the type configured to enable multiple Trendelenburg positions or Lateral Oblique positions characterized by the operating table OT positioned to orient the patient P at a steep angle greater than about 30 degrees.

Figures 3, 4:
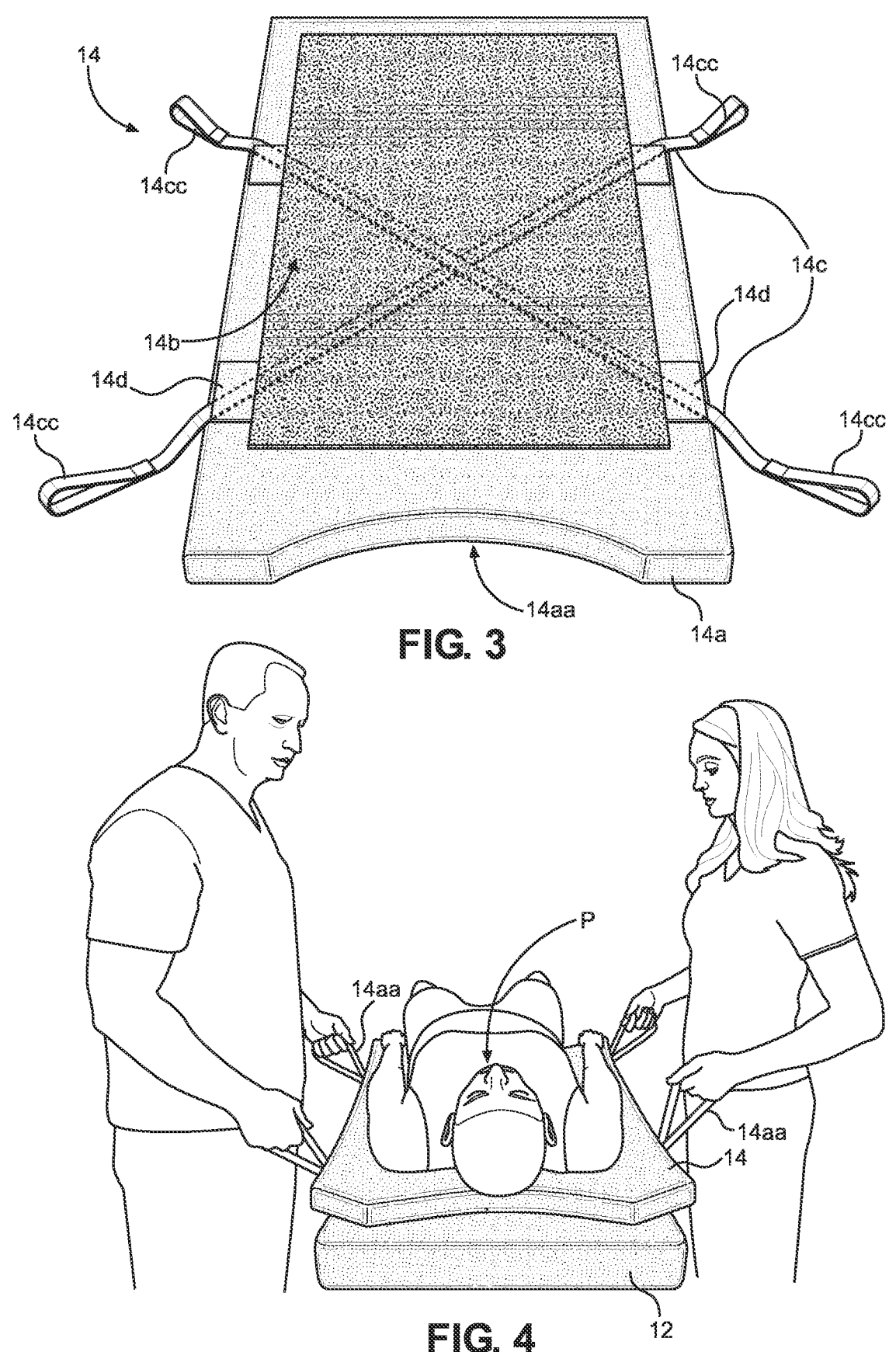
FIGS. 3-4 show a positioning pad component of the patient positioning system.

With continued reference to FIGS. 1 and 2 and with additional reference to FIG. 3, the flat mattress pad base 12 may be placed on top of the operating table OT in replacement of a conventional mattress of the operating table OT. The pad base 12 may include a cutout 12a at the foot end to conform to a foot end of the operating table OT. In this regard, it will be understood that the pad base 12 may be of universal sizing to fit a variety of operating tables or custom configured for a specific operating table.

With reference to FIGS. 3 and 4, the positioning pad 14 is configured to be located on top of the pad base 12. However, it will be understood that the positioning pad 14 may be used directly on the operating table OT or a conventional mattress of the operating table OT or other patient support surface such as a bed. The positioning pad 14 includes a lower pad 14a made of a flexible high-density polyurethane foam, with a foot-end of the lower pad 14a having a crescent-shaped cutout 14aa.

A smaller textured non-slip polymeric sheet 14b is centered on and glued to the pad 14a. The polymeric sheet 14b is preferably a thin sheet made of polyvinyl chloride having a high coefficient of friction.

A pair of cross straps 14c having handles 14cc on the ends thereof are centrally secured to the top of the lower pad 14a so that the straps 14c cross at the center of the lower pad 14a and locate the handles 14cc at spaced apart locations on the sides of the pad 14 for lifting and moving of a patient located on the pad 14, as shown in FIG. 4. Rubber or polymeric patches 14d are located adjacent the locations of the handles 14cc and adhesively secured to the upper surface of the lower pad 14*a* with the straps 14*c* extending underneath the patches 14*d* to buttress and reinforce securement of the straps 14*c* to the lower pad 14*a*.

Figure 6A:
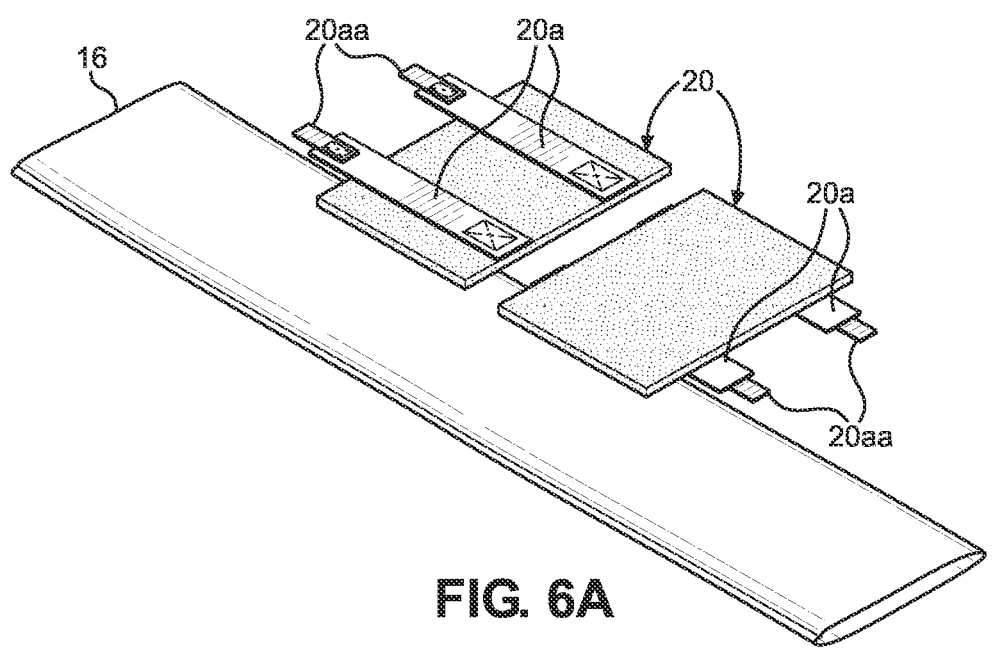
FIGS. 6A-6F show arm positioner components of the patient positioning system.
Figure 6B:
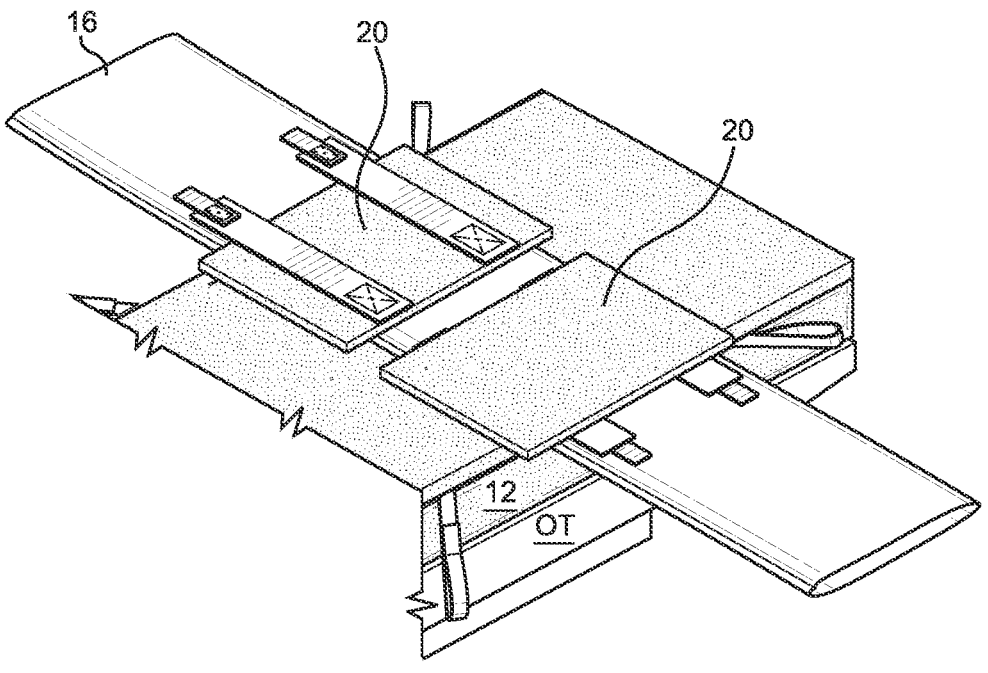
Figure 6C:
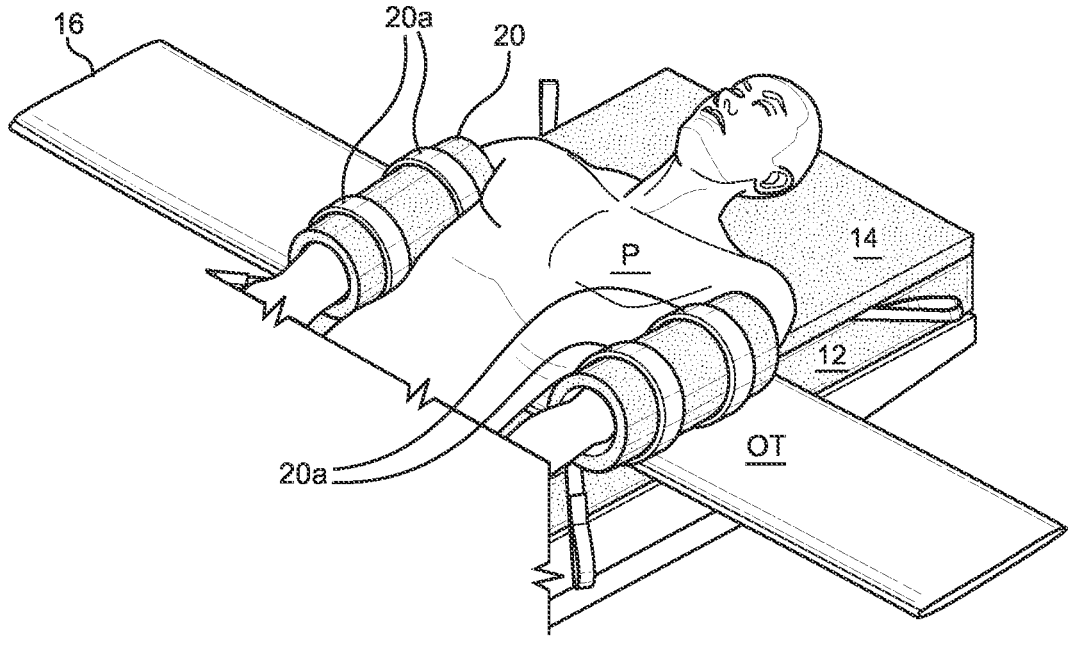

As shown in FIGS. 1 and 6*c*, the lift sheet 16 is located across the width of the operating table OT to be positioned to extend underneath the lower back of the patient P. The lift sheet 16 is made of a soft, cotton fabric sheet that is sewn in half to increase strength. The lift sheet 16 is generally configured to be about 12 inches wide by 84 inches long. The lift sheet 16 is soft and flexible and would drape down over the edge of the operating table OT but is shown extended to demonstrate that it is located on top of the patient pad 14 and extends below the lower back of the patient P. As explained more fully below, the lift sheet 16 may be used for lifting and positioning the patient and ultimately located and configured to hold the arms within the arm positioners 20 against the patient's body.

Figure 5A:
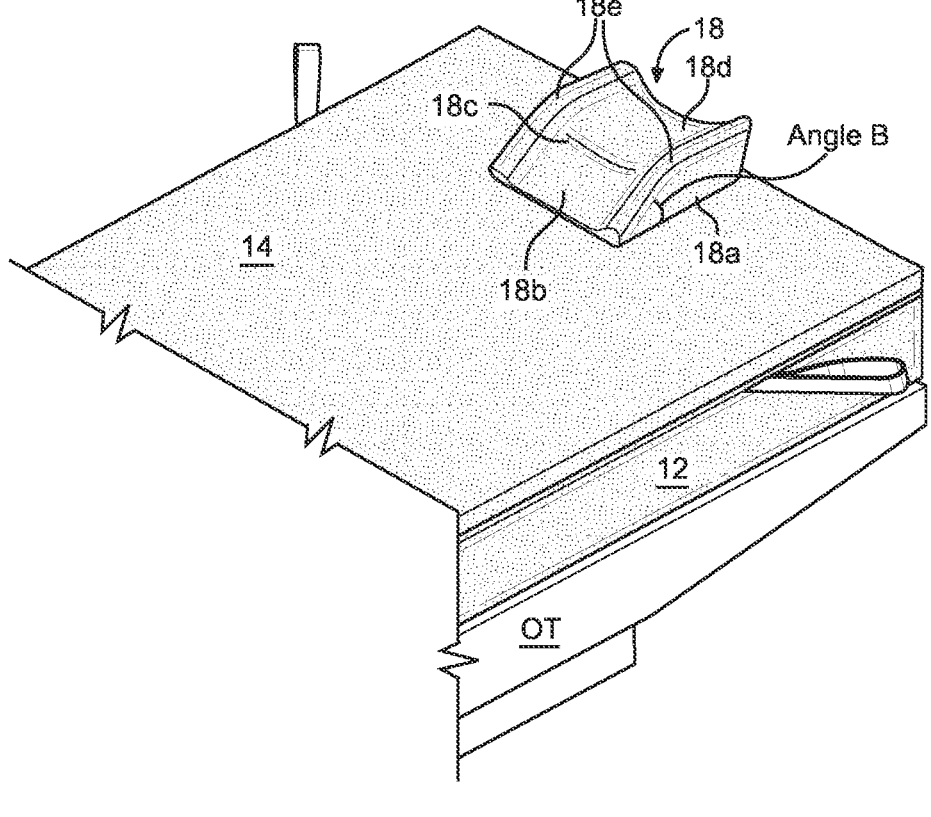
FIGS. 5A-5B show a head positioner component of the patient positioning system.
Figure 5B:
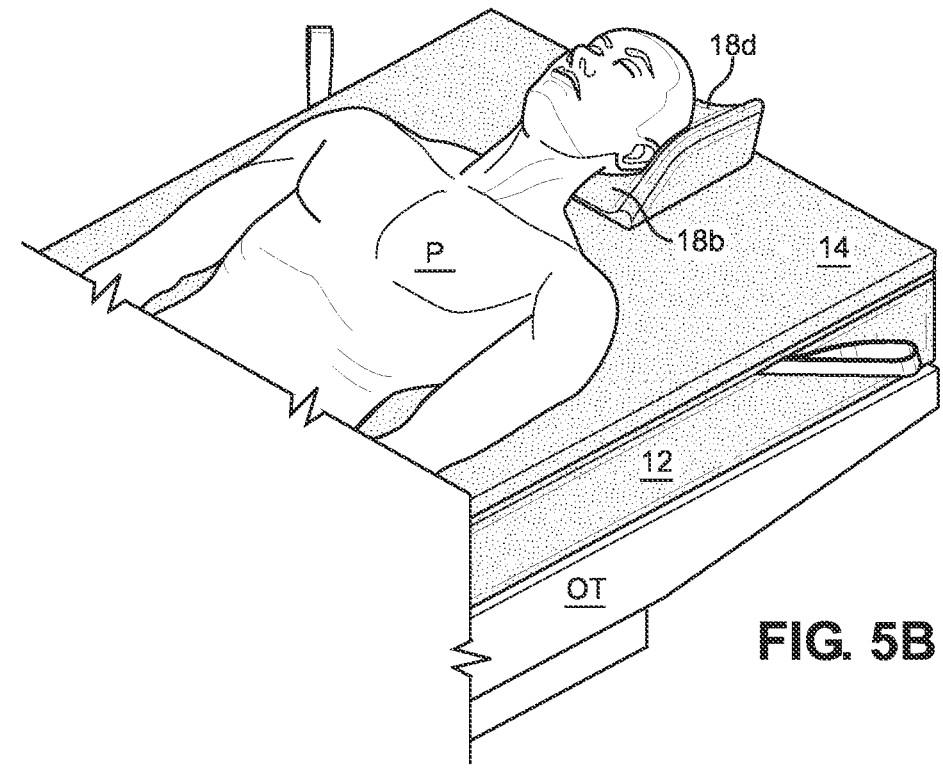

With reference to FIGS. 1 and 2, and additional reference to FIGS. 5A-5B, the head positioner 18 is made of a flexible high-density polyurethane foam and configured to receive the neck and head of the patient. The head positioner 18 has a planar base 18*a* that sits on the upper surface of the pad 14. An inclined neck trough 18*b* is angled upwardly from the base 18*a* at an angle B of from about 30 degrees to about 60 degrees, most preferably about 45 degrees. An uppermost portion of the inclined neck trough 18*b* transitions to provide a smooth curve 18*c* that meets and merges with a generally horizontal head trough 18*d*. The neck trough 18*b* cradles the neck of the patient and the head trough 18*d* cradles the head of the patient. The trough shape of the head positioner 18 includes a pair of upstanding walls 18*e* that extend along the opposite sides of the head positioner 18 to further stabilize the neck and head of the patient P. Together, these features cooperate to provide desired and stable positioning of the head and neck of the patient.

With additional reference to FIGS. 1, 2 and 6A-6F, the arm positioners 20 are configured as flat rectangular pieces of a flexible high-density polyurethane foam configured to surround and encase the arm. Each arm positioner 20 is generally flat and configured to be wrapped around an arm of the patient and releasably secured as by hook and loop material or other releasable fastener.

As shown, each of the arm positioners 20 has a pair of straps 20*a* located on the exterior adjacent the ends of the length of the arm positioners 20. The straps 20 extend around the outside and releasably secure. In this regard, distal or free end 20*aa* of the strap 20*a* may have hook/loop material thereon and the exterior of the strap 20*a* has loop/hook thereon to releasably mate and enable incremental adjustment.

The arm positioners are oriented so that the straps 20*a* are on the bottom adjacent to and face the patient pad 14, with the arm of the patient over the opposite upwardly facing surface. As will be noted, one of the arm positioners 20 is flipped in FIGS. 6A-6B to show the straps 20*a*.

To install the arm positioner 20 onto one of the arms of the patient, the arm of the patient P is placed over the flat surface of the arm protector 20 and the arm protector 20 is curled around the arm of the patient P and the straps 20*a* engaged to hold the arm protector 20 around the arm of the patient P, as shown in FIG. 6C.

If additional adjustment of the position of the patient P is needed at this point, the lift sheet 16 as positioned in FIG. 6C may be used to adjust the position of the patient P by grasping each end of the lift sheet 16 and lifting to unweight the back of the patient P and adjust the position of the patient P.

Figure 6D:
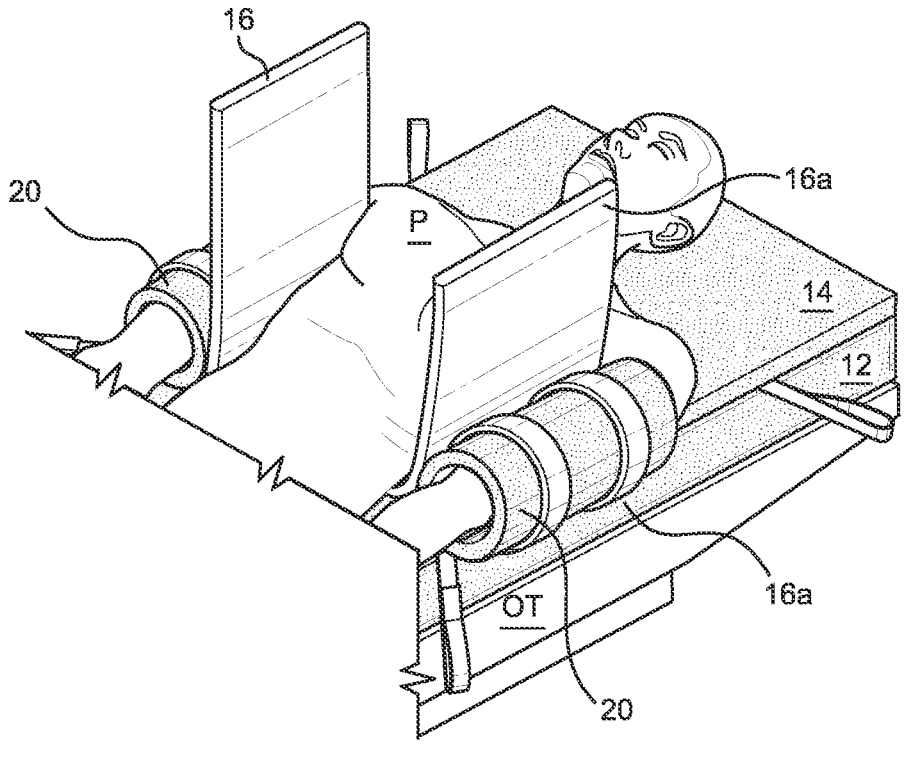
Figure 6E:
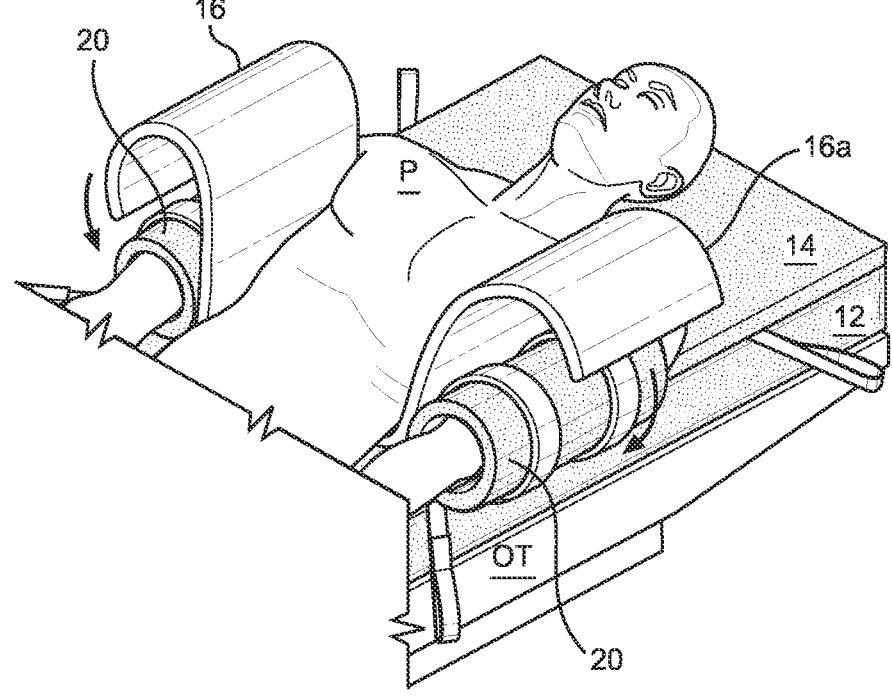
Figure 6F:
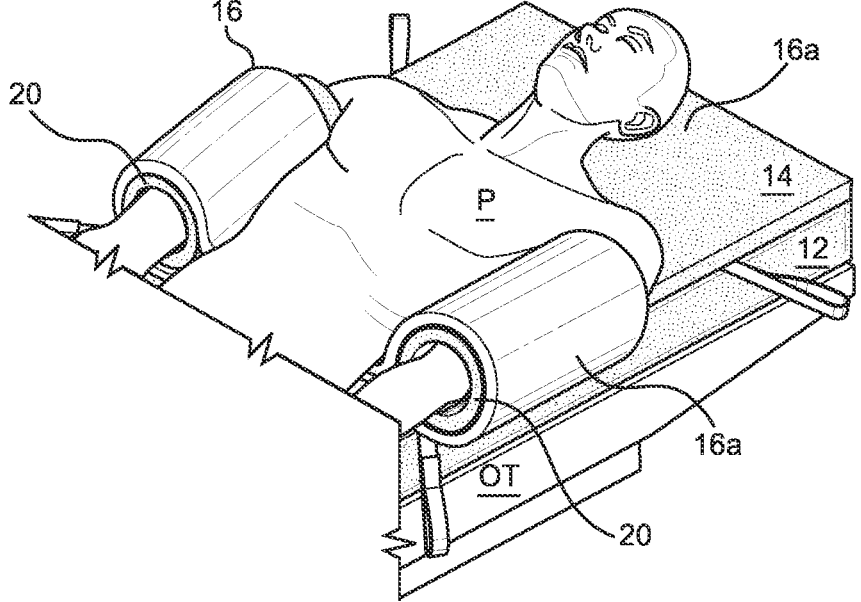

Next, as shown in FIGS. 6D-6F, the lift sheet 16 is positioned relative to the arm positioners 20 to secure the patient's arms in position. As shown in FIG. 6D, each end 16*a* of the lift sheet 16 is pulled up between the arms of the patient P and the torso of the patient P. Next, as shown in FIG. 6E, the ends 16*a* of the lift sheet 16 are wrapped over and around the arm positioners 20. Finally, as shown in FIG. 6F, the ends 16*a* of the lift sheet are passed back under the arms protectors 20 and the ends 16*a* of the lift sheet 16 are each tucked under the lower back or sacrum of the patient to securely and snugly hold the lift sheet 16 around the arm positioners 20 and restrain the arms of the patient. In addition, the thickness of the underlying portion of the lift sheet 16 plus the thickness of the tucked ends 16*a* of the lift sheet 16 support the sacrum at the base of the spine and offload pressure from the sacrum. As installed, the arm positioners 20 with the lift sheet 16 are restrained from movement by the weight of the patient P to restrain the patient P and the arms of the patient P against movement.

Figures 7A, 7B, 7C:
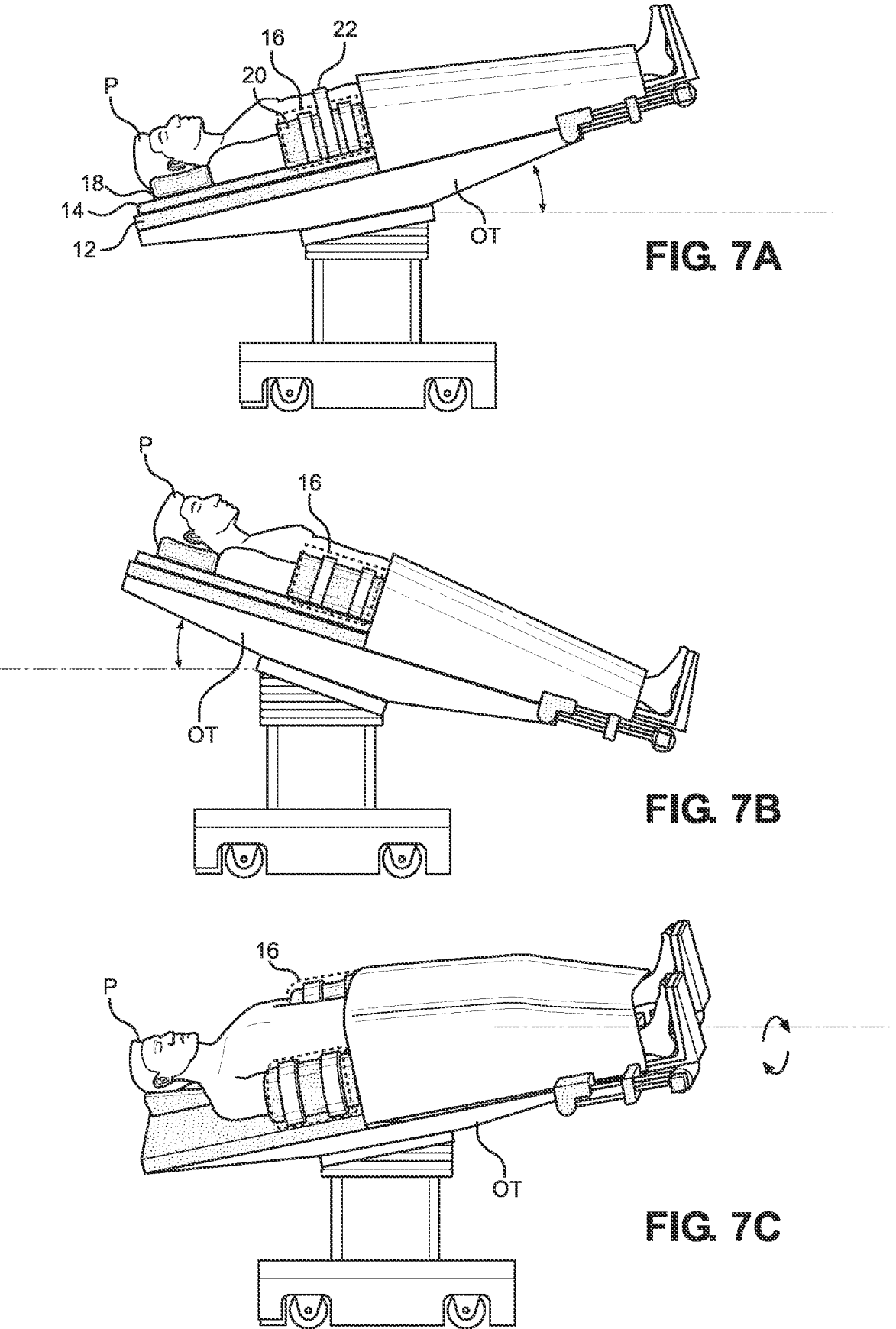
FIGS. 7A-7C depict use of the patient positioning system in various steep angle surgical procedures.

Once the patient P is securely and desirably positioned using the pad 14, the lift sheet 16, the head positioner 18, and the arm positioners 20, the body strap 22 is secured around the patient P, preferably around the arm positioners 20 and the operating table OT to further secure the patient against movement. As depicted in FIGS. 7A-7C, the positioning system 10 is effective to secure the patient P against movement in multiple steep angle positions, such as Trendelenburg positions or Lateral Oblique positions in which the patient P is oriented at a steep angle greater than about 30 degrees. The lift sheet 16 is shown in dashed lines to enable view of the arm positioners 20.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated.

The invention claimed is:

1. A patient positioning system configured for positioning and supporting a patient against movement on an operating table, the positioning system comprising:

a pair of arm positioners each configured to be positionable about an arm of the patient when the patient is lying on the operating table, each of the arm positioners provided as a sheet material configured to be wrapped around one of the arms of the patient to position each of the arm positioners to snugly envelope one of the arms and having releasable fasteners to maintain the arm positioners in the wrapped configuration;

an elongate lift sheet configured to extend across the operating table and underneath the back of the patient, the lift sheet being positioned to have opposite ends thereof wrapped over and around the arm positioners and tucked back under the lower back or sacrum of the patient to securely and snugly hold the lift sheet around the arm positioners and restrain the arms of the patient; and a positioning pad positionable on top of the operating table and underneath the patient, the positioning pad having a lower pad made of a flexible foam and a non-slip polymeric sheet adhered on top of the lower pad, with a pair of cross straps secured on top of the lower pad and below the non-slip polymeric sheet for lifting and moving of the patient located on the positioning pad.

2. The patient positioning system of claim 1, wherein the lift sheet also supports the sacrum at the base of the spine of the patient and offloads pressure from the sacrum.

3. The patient positioning system of claim 1, wherein a foot-end of the lower pad has a crescent-shaped cutout.

4. The patient positioning system of claim 1, further comprising reinforcement patches secured to the upper surface of the lower pad with the straps extending underneath the patches to buttress and reinforce securement of the straps to the lower pad.

* * * * *